(12) United States Patent
Hitschrich et al.

(10) Patent No.: US 12,731,354 B2
(45) Date of Patent: Sep. 8, 2026

(54) METHOD FOR ANALYSING 3D MEDICAL IMAGE DATA, COMPUTER PROGRAM AND 3D MEDICAL IMAGE DATA EVALUATION DEVICE

(71) Applicant: KONINKLIJKE PHILIPS N.V., Eindhoven (NL)

(72) Inventors: Niklas Domenic Maria Hitschrich, Germany (DE); David Vincent Günther Hitschrich, Hannover (DE); Marcus Schreckenberg, Freising (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 77 days.

(21) Appl. No.: 18/697,132

(22) PCT Filed: Sep. 7, 2022

(86) PCT No.: PCT/EP2022/074807
§ 371 (c)(1),
(2) Date: Mar. 29, 2024

(87) PCT Pub. No.: WO2023/052057
PCT Pub. Date: Apr. 6, 2023

(65) Prior Publication Data

US 2024/0394996 A1 Nov. 28, 2024

(30) Foreign Application Priority Data

Sep. 30, 2021 (EP) .................................... 21200080

(51) Int. Cl.
*G06T 19/20* (2011.01)
*G06T 3/40* (2006.01)
(Continued)

(52) U.S. Cl.
CPC ................ *G06T 19/20* (2013.01); *G06T 3/40* (2013.01); *G06T 7/10* (2017.01); *G16H 30/20* (2018.01);
(Continued)

(58) Field of Classification Search
CPC ........... G06T 19/20; G06T 7/10; G16H 30/20; G16H 30/40
(Continued)

(56) References Cited

U.S. PATENT DOCUMENTS 6,480,732 B1 11/2002 Tanaka et al.
2005/0025384 A1 2/2005 Ming-Jeu
(Continued)

FOREIGN PATENT DOCUMENTS

WO WO-2017212063 A1 * 12/2017 ............. G06T 15/08
WO 2021043684 A1 3/2021
WO 2021259724 A1 12/2021

OTHER PUBLICATIONS

International Search Report and Written Opinion for PCT/EP2022/074807; Mailing date: Jan. 5, 2023, 17 pages.
(Continued)

*Primary Examiner* — Thomas J Lett

(57) ABSTRACT

A method for displaying and analysing 3D medical image data comprising is provided. The method comprising receiving 3D medical image data of an anatomical structure; generating a 3D rendering (1) of the anatomical structure based on the 3D medical image data; displaying the 3D rendering (1) to a user (20) in a visualisation environment
(Continued)

(10); receiving a user's command indicative of a first point (4) on or within the 3D rendering (1); providing an 2D-frame (2) at a position in the visualisation environment (10) in correspondence to the first point (4), wherein a first side of the 2D-frame (2) is facing the user (20); displaying a MPR-view (3) within the 2D-frame (2), wherein the MPR-view (3) is based on the 3D medical image data at the position of the 2D-frame (2) and is sized so as to correspond to the size of the 2D-frame (2); and providing a transparent cropping body (9) between the user (20) and the first side of the 2D-frame (2) so as to partly crop the 3D rendering (1). Further, a computer program and a 3D medical image data evaluation device is provided.

15 Claims, 11 Drawing Sheets

(51) Int. Cl.
*G06T 7/10* (2017.01)
*G16H 30/20* (2018.01)
*G16H 30/40* (2018.01)

(52) U.S. Cl.
CPC ..... *G16H 30/40* (2018.01); *G06T 2219/2004* (2013.01); *G06T 2219/2016* (2013.01)

(58) Field of Classification Search
USPC .......................................................... 345/419
See application file for complete search history.

(56) References Cited

U.S. PATENT DOCUMENTS

2007/0229500 A1 10/2007 Engel et al.
2009/0148020 A1 6/2009 Sugiura
2012/0308095 A1 12/2012 Engel et al.
2012/0313943 A1 12/2012 Tsukagoshi et al.
2015/0042657 A1 2/2015 Smith-Casem et al.
2019/0122361 A1* 4/2019 Lilliestråle ............. A61B 34/10
2019/0272667 A1* 9/2019 Roundhill ............... G06T 19/00
2022/0130046 A1 4/2022 Schreckenberg et al.

OTHER PUBLICATIONS

Vogt, S. et al., "An AR System with Intuitive User Interface for Manipulation and Visualization of 3D Medical Data," Medicine Meets Virtual Reality 12, vol. 98, pp. 397-403.
Deng, S. et al., "A Virtual Reality System for Improved Image-based Planning of Complex Cardiac Procedures," J. Imaging, 2021, vol. 7, 16 pages.
Narang, A. et al., "Virtual Reality Analysis of Three-Dimensional Echocardiographic and Cardiac Computed Tomographic Data Sets," Journal of the American Society of Echocardiography, 2020, vol. 33, Issue 11, pp. 1306-1315.
Kaufmann, A. et al., "Overview of Volume Rendering," Visualization Handbook, 2005, p. 127.
Hitschrich N, et al.: "Comparison of measurements made on volume rendered 3D virtual reality models versus conventional 3D software," 2019 ASE 30th Annual Scientific Sessions, 2019, 1 page.

* cited by examiner

METHOD FOR ANALYSING 3D MEDICAL IMAGE DATA, COMPUTER PROGRAM AND 3D MEDICAL IMAGE DATA EVALUATION DEVICE

CROSS-REFERENCE TO PRIOR APPLICATIONS

This application is the U.S. National Phase application under 35 U.S.C. § 371 of International Application No. PCT/EP2022/074807, filed on Sep. 7, 2022, which claims the benefit of European Patent Application No. 21200080.6, filed on Sep. 30, 2021. These applications are hereby incorporated by reference herein.

FIELD OF THE INVENTION

The present invention relates to a method for analysing 3D medical image data, to a computer program and to a 3D medical image data evaluation device.

BACKGROUND OF THE INVENTION

There are a plurality of modalities that can acquire three-dimensional (3D) medical image data of the human or animal body like 3D ultrasound (US), computed tomography (CT), magnetic resonance imaging (MRI), 3D echocardiographic (3DE) and cardiac computed tomographic (CCT) etc. One way to display the acquired 3D medical image data is to visualise it as a 3D volume generated by rendering the 3D image data. Therefore, the visualized 3D volume may be also referred to as 3D rendering. The 3D rendering may be displayed on two-dimensional (2D) screens, in a virtual reality environment (VR) or in an augmented reality environment (AR). Particularly, the upcoming development of consumer-friendly AR/VR headsets allow the user to step into a virtual space where he sees the 3D volume stereoscopically in "true 3D" using a headset with two separate screens and two separately calculated images for his left and right eye. In combination with very precisely tracked hand controllers or hand tracking this allows very natural interaction with 3D content. For medical 3D data imaging, and compared with conventional imaging, VR analysis is associated with faster navigation and accurate measurements with lower variability.

In any case, 3D volume rendering or navigation with multiplanar reconstruction (MPR) planes are the two most common ways to look at medical 3D data. MPRs are regarded as being the "ground-truth" of the dataset, display certain planes cut through the 3D volume and are used to make measurements. On the other hand, while 3D volume renderings in combination with VR analysis provide a stereoscopic visualization of the dataset, measurements in 3D volume renderings are very sensitive to the chosen volume threshold, potentially leading to incorrect measurements and wrong clinical conclusions.

In virtual reality environments the volume rendering and MPRs may be simultaneously displayed. However, the problem is that an opaque MPR plane often blocks the view of the 3D volume (i.e. anatomical structures) behind it or vice versa.

It would therefore be desirable to have a solution that optimally combines the visual overview capabilities of a 3D volume together with the precise measurement capabilities of MPR.

US 2007 229500 A1 shows a method to render MPR images in the context of the surrounding material using a combination of direct volume rendering and MPR rendering. By shifting the MPR, the user can interactively change an incision area to reveal the interior of the image volume.

WO 2017/212063 A1 shows a medical imaging and visualisation system that provides a user interface enabling a user to visualize a volume rendering for a three-dimensional data set and to manipulate the volume rendering to dynamically select a MPR plane within the 3D data set for generating a B-mode image at the selected MPR plane.

US 2012/0308095 A1 shows a system for adjusting the visualisation of volume data of an object as an image with regard to diagnostically relevant medical information relating to the environment of a region under investigation. Accordingly, at least one slice region is specified based on slice information within the volume data. A first mapping of the volume data is used for visualizing the at least one slice region on a display. A second mapping different from the first mapping is used for visualizing a region adjacent to the slice region.

However, the problem still remains that the opaque MPR plane often blocks the view of the anatomical structures behind it, which immediately increases the risk of setting an incorrectly positioned MPR plane and thus incorrect measurements.

OBJECT OF THE INVENTION

Therefore, it is an object of the present invention to provide a holistic visualisation of 3D medical image data while allowing precise measurements or analysis of the dataset.

SUMMARY OF THE INVENTION

The object is solved by a method for analysing 3D medical image data including the features of claim 1, by a computer program including the features of claim 14 and by a 3D medical image data evaluation device including the features of claim 15.

According to an aspect of the present invention a method for analysing 3D medical image data is provided, the method comprising:

- receiving 3D medical image data of an anatomical structure;
- generating a 3D rendering of the anatomical structure based on the 3D medical image data;
- displaying the 3D rendering to a user in a visualisation environment;
- receiving a user's command indicative of a first point on or within the 3D rendering;
- providing an 2D-frame at a position in the visualisation environment in correspondence to the first point, wherein a first side of the 2D-frame is facing the user;
- displaying a MPR-view within the 2D-frame, wherein the MPR-view is based on the 3D medical image data at the position of the 2D-frame and is sized so as to correspond to the size of the 2D-frame; and
- providing a transparent cropping body between the user and the first side of the 2D-frame so as to partly crop the 3D rendering.

In contrast to the state of the art, the present invention provides a different approach of using both a 3D rendering and a MPR-view to analyse 3D medical image data. While in the prior art either a 3D rendering or a MPR-view is used to analyse medical image data, in the present invention both the 3D rendering and the MPR-view are simultaneously used to holistically analyse the 3D medical image data. That is, in the prior art both methods were alternately used. Accordingly, the advantages of each analysing method can be combined in order to improve the analysing process of 3D medical image data.

In particular, the 2D-frame in which the MPR-view is depicted may be positioned anywhere in the 3D-rendering without completely overlaying the 3D rendering. In particular, the 3D rendering around the 2D-frame may still visible (i.e. the 3D rendering is not completely hidden by the 2D-frame). Accordingly, the user can still get a spatial overview of the 3D medical image data by looking at the 3D rendering. This is important because the position of the MPR-view within the 3D rendering is critical for clinical decisions and is highly error-prone, as a high level of experience and spatial imagination is required to select the correct position of the MPR-view within the 3D rendering. According to the present invention the user may have an improved orientation due to seeing both the MPR-view and the 3D rendering so as to correctly position the 2D-frame. Preferably, the area covered by the MPR-view (i.e. within the 2D-frame) is smaller than the 3D rendering and represents a very specific section of the 3D medical image data. In other words, the visible area of the MPR-view is limited to the area of the 2D-frame.

For example, the user may rotate or move the 3D rendering for getting a better orientation and for accurately positioning the 2D-frame within the 3D-rendering. In other words, the user may orient himself using the 3D-rendering and may thus accurately provide the 2D-frame at an appropriate position of the 3D rendering to analyse this region (e.g. a region of interest) of the 3D rendering in detail. Due to the cropping body, the user may have a largely unobstructed view of the MPR-view. That is, the 3D-rendering may be cropped only partly such that the user may still see a part of the uncut 3D-rendering. That is, the 3D-rendering may be cropped so as to provide a largely unobstructed view of the MPR-view within the 2D-frame. Accordingly, the analysis of 3D medical image data may be simplified and made more intuitive, as the user can view both the 3D rendering and the MPR-view at the same time, so that he still has an overview of the entire 3D rendering while being able to analyse the MPR-view in detail.

3D medical image data may be provided as a digital image, e.g. in DICOM standard, i.e. containing a three-dimensional array of voxels, each voxel containing a grey scale value. Such 3D medical image data have typically been obtained from a field of view containing the anatomical structure using a medical imaging modality, such as MR, computed tomography (CT), positron emission tomography (PET) or ultrasound (US), for example. When the anatomical structure is the heart, ultrasound and in particular transesophageal echocardiography (TEE) may be advantageously used. For example, the 3D medical image data may be acquired over a time span so as to obtain four-dimensional (4D) medical image data, wherein the fourth dimension is the time. In this case, one 3D image from the 4D medical image data may be also called a "frame" in the following. The 3D images may be acquired with a frame rate of e. g. 5-100, preferably 20-60 images per second, so as to allow a smooth representation of a dynamically moving anatomical structure. The time period is usually at least one cycle of the cyclical movement, e. g. at least one heartbeat. The 3D medical image data can be received directly from a modality that has acquired the medical image data or from a clinical image database.

The generating of the 3D rendering may use an adjustable threshold to display only certain voxels within the threshold range. Colour shading and special lightning techniques may be used to create the impression of depth on a 2D screen. The 3D rendering may be generated by a volume rendering process that may be performed using any volume rendering technique known in the art, for example as described in US 2005/0253841 A1, incorporated herein by reference. Usually, one needs to define a camera position and a viewing direction in space to perform volume rendering. This position may correspond to the viewing position of the user. Also, some techniques define the opacity and colour of every voxel. A common technique is volume ray casting. In this technique, a ray is generated for each desired image pixel. Using a simple camera model, the ray starts at the centre of projection of the camera (usually the viewing position or eye point) and passes through the image pixel on an imaginary image plane floating between the camera and the volume to be rendered. Then the ray is sampled at regular or adapted intervals throughout the volume. The data is interpolated at each sample point, a transfer function applied to form an RGBA sample, the result added onto the accumulated RGBA of the ray, and the process repeated until the ray exits the volume. The process is repeated for every image pixel on the screen to form the completed image. The 3D rendering may be considered as a visualised three-dimensional volume.

The volume rendering may be performed by techniques described in "The Visualization Handbook", edited by Charles H. Hansen and Christopher R. Johnson, Elsevier Butterworth Heinemann 2005, especially in the Chapter "Overview of Volume Rendering" by Arie Kaufmann starting on p. 127, and which is incorporated herein by reference.

The visualisation environment may be defined by a visualisation coordinate system having the coordinates X, Y and Z (world coordinates). In addition, the 3D rendering may be defined in an object coordinate system having the coordinates X', Y' and Z' (object coordinates). Moreover, the 3D medical image data may be defined with respect to an original coordinate system having the coordinates X", Y" and Z" (3D medical image coordinates). The coordinate systems may be shifted with respect to each other. As a result, objects such as the 3D rendering, the 2D frame, a surface mode etc. may be defined in separate coordinate systems so as to be shifted with respect to each other. On the other hand, the viewing position of the user may be defined by the visualisation coordinate system.

The visualisation environment may be a VR/AR-visualisation environment or a non-VR visualisation environment. In a non-VR visualisation environment, an input tool used by the user may be a keyboard, a pointing device such as a mouse, trackball, touchpad or touch-sensitive display, which are usually used in conjunction with an interactive panel comprising buttons, sliders etc. viewed on a screen. Such buttons or sliders may for example be actuated by the user with his finger or a pointing device, e.g. the user may move a cursor on a screen to actuate the input tools. By such input tools, the user may for example zoom in and out of the visualisation, adapt visualisation parameters/settings such as a 3D rendering threshold, smoothing, lighting and contrast, start and hold a cine mode, and perform measurements on the 3D rendering and/or the MPR-view. In a particularly useful embodiment, the input tool allows a user to set points and to take measurements on the anatomical structure. For example, the user may select two points on the 3D rendering, and/or the MPR-view and the distance between such points will automatically be calculated. This feature is useful when planning interventions, e.g. choosing implants. In some embodiments, the user may be able to "grab" a visualised object by means of a pointing device, i.e. a mouse or a touch on the touch-sensitive display, and thereby move or tilt it. The object may be a simulated implant or other objects that have to be fitted individually to a patient.

In a VR environment, such input tool is preferably realised by a virtual controller allowing a user at least to grab and move an object within the virtual reality environment by hand gestures. "Move" in this context may also mean rotate. The VR controller may also allow a user the change the size and/or shape of VR objects. Further, the VR controller may include buttons or sliders by which the user may take selections. In a VR environment, a user wearing a VR headset and holding at least one VR controller in one hand (preferably a VR controller in each hand) sees in the VR environment a static or dynamic visualisation of the anatomical structure consisting of the 3D rendering and the MPR-view. Preferably, he can also see the controllers at the positions and orientations corresponding to the current hand positions and orientations. Thus, the VR environment provides the possibility for the user to move the controllers towards the visualisation, grab it by pressing a particular button, and move and/or rotate the visualised object with the movement of his hands, like he would with a real-world object. Thereby, the users have 18 degrees of freedom (six degrees of freedom, namely three rotational and three translational degrees of freedom for the VR headset and each of the two VR controllers) to correctly and intuitively view and analyse the visualised object. This closely resembles the natural way of interacting with objects.

For example, by any of the above user's actions, the command may be issued by a user who is analysing the 3D medical image data. The command may be:

a) a start of a workflow of analysing the 3D medical image data,
b) moving a pointer of a pointing device (e.g. a mouse, a VR-controller, touchpad, trackpad, trackwheel etc.) to a specific position within the visualisation environment and pressing a bottom and/or linger at the position for a predefined time span,
c) a gesture made by the user, and/or.
d) pressing a bottom (e.g. a virtual bottom).

In any case the command may result in a definition of a first point having a spatial position within at least one of the coordinate systems defined above. For example, the first point may be defined within the original coordinate system X", Y" and Z", which may be then translated into the object coordinate system X', Y' and Z'. That is, the first point may be positioned at predetermined coordinates within the visualisation environment. Preferably, the coordinates define a spatial position (x-, y-, z-coordinates) within the visualisation environment.

The case a) may include the start of executing the method on a computer or other machine including a processor. That is, the command may be a command that starts the execution of the method. In this case the first point indicated by the user may have a predetermined position defined within the visualisation coordinate system by coordinates X, Y and Z within the visualisation environment. Preferably, the coordinates define a spatial position within the visualisation environment. This enables the user to perform an analysis immediately when starting to execute the method. This makes the workflow particularly user-friendly. In addition, the workflow may be a measurement workflow that is activated by the user when he wants to measure a distance, an area, a surface, etc. of the anatomical structure. Thus, the first point (and therefore the 2D-frame) may be only provided in the visualisation environment in case the user wants to execute a specific workflow (e.g. to execute a measurement). Until such a command, there may be no 2D-frame within the visualisation environment and the user may view the full 3D rendering without any obstruction. Therefore, the user may get an impression of the entire 3D rendering before starting to execute a specific workflow. The initial position of the first point may be set prior to starting the method.

Case b) may be regarded as the active issuing of a command directly indicative of the position of the first point. For example, the user may move a controller (in the case of a VR environment) or any other pointing device to a specific spatial position within the visualisation environment and may press a button on the controller when the position is reached. Alternatively, the user may move a pointer of a pointing device (mouse, trackpad etc.) to such position and activate a button. Accordingly, the first point may be defined within at least one of the coordinate systems. This allows the user to actively control when the command is given and where the first point is placed within the visualisation environment. That is, the spatial position where the first point should be defined may be directly and individually controlled by the user. Therefore, an individual work process may be provided.

Case c) may be a predetermined gesture (e.g. a head nod, a movement with one or two arms, etc.) by the user which may be recognised by a system by which the method is executed. Accordingly, there may be provided a receiver in order to recognise such gestures of the user. In case the system includes a VR-headset, the receiver may be provided in the headset. Alternatively or additionally, there may be provided a camera which is configured to receive gestures by the user. In case c), the first point specified by the user can be a given spatial position within the visualisation environment or the spatial position can be derived by the gesture itself. For example, the gesture can specify a spatial position within the visualisation environment.

Depending on the first point, the 2D-frame may be provided within the visualisation environment. That is, based on the first point a spatial position of the 2D-frame may be directly or indirectly derived from the position of the first point. The 2D-frame may be provided on or within the 3D rendering. In other words, the 3D rendering may depict the anatomical structure included in the 3D medical image data. Thus, the 3D rendering may be a closed volume having an outline. The 2D-frame may be on the surface of the 3D rendering (i.e. on the surface of the closed volume), within the 3D rendering, outside of the 3D rendering or partly inside and partly outside of the 3D rendering.

In case d) the user may hit a virtual button such as to issue a first point without directly defining a spatial position of the first point. In this case, the first point may be defined by coordinates X, Y and Z in the visualisation coordinate system first. For example, this may be done if the user does not know where to exactly position the 2D-frame within the 3D rendering and first wants to have a MPR-view at a predetermined position to find such position within the 3D rendering.

The 2D-frame may have an extension only in two dimensions. That is, the 2D-frame may have no extension in the third direction (e.g. the depth- or z-direction). Alternatively, the 2D-frame may have the same thickness as the MPR-view (e.g. the same thickness as the MPR-slice). In other words, the 2D frame may have the same dimensions as the MPR-view. The 2D-frame may be considered as a picture frame, wherein the picture may be the MPR-view and which may be surrounded by a thin line or rim to better indicate the position of the 2D-frame. There may be at least four implementations for providing the 2D-frame within the visualisation environment which may be combined with any of the above a) to d):

I) The 2D-frame may be centred on the first point indicated by the user's command. That is, the 2D-frame may be positioned such that the barycentre of the 2D-frame lies on the position of the first point.

II) As above, the 2D-frame may be centred on the first point indicated by the user's command. Further, the first point may have a fixed spatial position within the same coordinate system as the 3D rendering (e.g. within the object coordinate system). In other words, if the 3D rendering is moved and/or rotated the first point and thus the 2D-frame is moved too. That is, three degrees of freedom (up and down, back and forward, left and right) of the 2D-frame may be fixed with respect to the 3D rendering. However, the 2D-frame can still be moved in three degrees of freedom, i.e. roll, yaw and/or pitch. This is advantageous when a specific part of the anatomical structure is to be examined. Accordingly, the user may position the first point at such a section on his command and the 2D-frame is provided at that particular position regardless of the rotation or movement of the 3D rendering. In addition, the 2D-frame may be positioned within the visualisation environment two points may be fixed with respect to the object coordinate system. One of these points may be the first point, the second point may be defined such that the 2D-frame is facing the user. Accordingly, the 2D frame can only be moved in the rotational degrees of freedom. This makes it particularly easy for the user, as he can immediately start analysing the MPR view within the 2D frame.

III) As above, the 2D-frame may be centred on the first point indicated by the user's command. Further, a distance between the user and the 2D-frame may be determined. Such distance can be the distance of the virtual position of the user to the 2D-frame. In particular, the distance may be the distance between the user and the barycentre of the 2D-frame or may be a mean distance between all points of the 2D-frame and the user. In other words, the 2D-frame may be defined in the same coordinate system as the viewing position of the user (e.g. in the visualisation coordinate system). In the further examination process the distance between the user and the 2D-frame may be fixed. This means that the 2D-frame can be considered as the user's Head Up Display, because regardless of whether the user changes his position in relation to the 3D rendering, the 2D-frame may always have the same distance from the user. This allows for very intuitive navigation within the visualisation environment and is particularly advantageous when viewing large 3D medical image data. This is particularly useful in combination with the above d).

IV) As above, the 2D-frame may be centred on the first point indicated by the user's command. The position of the 2D-frame may then be fixed to the coordinates of the visualisation coordinate system X, Y and Z. In other words, the 3D rendering may be moved, rotated etc. But the 2D-frame is fixed to the coordinates of the visualisation coordinate system X, Y and Z. In particular, the 3D rendering (being defined by the object coordinate system) can be dragged through the 2D-frame without affecting the position of the 2D-frame.

The 2D-frame may have a polygonal outer contour (e.g. a rectangle, cuboid, triangle etc.). Alternatively, the 2D-frame may have a rounded contour (e.g. a circle, ellipse etc.). Further, the 2D-frame may have a predetermined size. That is, the 2D-frame may enclose a predetermined two-dimensional space. The predetermined size may be manually set by a user prior to indicating the command or may be automatically set dependent on the size of the 3D medical image data. For example, the size may be set such that the 2D-frame covers at least 1 to 20%, preferably 4 to 10% of the area of the 3D rendering in an initial visualisation. The area of the 3D rendering may correspond to the area of the image plane onto which the 3D medical image data is rendered. Alternatively, the initial size of the 2D-frame may be 1 to 20%, preferably 4 to 10% of the area of one side of the cuboid corresponding to the 3D medical image data. As a result, the working flow can be smoothly executed because the 2D-frame may be automatically adapted to the 3D-medical image data.

In any case, the 2D-frame may be adaptable. That is, that the size and/or shape of the 2D-frame may be adjusted after the 2D-frame has been provided in the visualisation environment. For example, the user may increase or decrease the size and/or shape of the 2D-frame in order to sufficiently cover the region of interest by the 2D-frame, while the 3D rendering is sufficiently visible around the 2D-frame. Accordingly, the arrangement of the 2D-frame may be individually adapted to the preferences of each individual user.

Further, the 2D-frame may have a virtual handle. The handle may be a virtual control panel which may be also depicted within the visualisation environment. In particular, the user may change further settings of the 2D-frame by operating the virtual control panel. For example, visualisation properties of the MPR-view may be set via the virtual control panel (e.g. brightness, contrast etc.). Using the handle, the user may change the position of the 2D-frame within the visualisation environment. In other words, the user can virtually grasp the handle and freely move the 2D-frame in any of the three dimensions within the visualisation environment. For example, the user may move the 2D-frame through the 3D rendering back and forth, up and down, and to the right and to the left. In addition, the user may additionally or alternatively move the 2D-frame using all three rotational degrees of freedom.

The 2D-frame is facing the user such that the user may see what is depicted within the 2D-frame (e.g. the MPR-view). That is, the 2D-frame is not oriented such that the user only sees one edge of the 2D-frame. Preferably, the 2D-frame is automatically oriented upon provision thereof such that it is facing the user. There may be an initial orientation of the 2D-frame which may be always the same when the 2D-frame is provided. The initial orientation may be predetermined by each user. That is, several users may individually set their own orientation of the 2D-frame prior to starting the analysing process. Accordingly, the method may be individualised according to preferences of each user. Then, the orientation of the 2D-frame may be provided depending on the user who is executing the analysing process. Further, the orientation may be adjusted by the user in real time while the user is analysing the 3D-medical image data. This allows the user to set up their field of view to best suit their personal preferences. For example, initially one rotational degrees of freedom (i.e. roll) may be fixed or only moveable in a range between 0 and 5°. That is, the 2D frame can be movable in two rotational degrees of freedom (i.e. yaw and pitch). Accordingly, usability can be improved as the user has a better overview when the 2D frame does not move randomly. Especially, in case the 2D-frame has a non-circular shape, a workflow may be more efficient.

A MPR-view may be displayed within the 2D-frame. The MPR-view may be directly derived from the 3D medical image data at the specific position of the 2D-frame. That is, if the 2D-frame is moved relative to the 3D rendering (and/or relative to the 3D medical image data) the MPR-view may be updated based on the 3D medical image data. The MPR-view may display all grey values (or interpolates grey values) of a plane cut through in the 3D medical image data at the position an orientation of the 2D-frame and can be seen as the "ground-truth" of the 3D medical image data. That is, in the MPR-view no information can be lost due to different display adjustments like the threshold on the 3D rendering. As a result, the MPR-view may correspond exactly to the 3D medical image data acquired from a patient. Consequently, measurements made in the MPR-view are based on the best available information. The MPR-view may be generated by multiplanar reconstruction which may be a process of converting 3D medical image data from one anatomical plane (usually transverse) to other (orthogonal or oblique) planes usually using interpolation, preferably nearest-neighbour interpolation, of pixel values. It can be used for thin slices as well as projections. For example, the MPR-view may be appropriately suited for depicting the anatomical structure of the bronchi as they do not lie orthogonal to the direction of the scan. Also, curved-plane MPR-views may be used for the evaluation of vessels. This type of reconstruction helps to straighten the bends in a vessel, thereby helping to visualise whole vessel by a MPR-view, or multiple MPR-view. After a vessel has been "straightened", measurements like cross sectional area, length can be made. It is very helpful in preoperative assessment of a surgical procedure. Further, the MPR-view may be opaque. That is, the user may not see what is behind the MPR-view.

In other words, the MPR-view may be used to view specific portions of the 3D medical image data in greater detail. The MPR-view may include said anatomical feature, but preferably not much more than the anatomical feature of interest, i.e. the MPR-view is as small as possible and just big enough to enclose the feature of interest. In other words, the position, size and/or shape of the MPR-view (i.e. also of the 2D-frame) may be adapted to match the position, size, orientation and/or shape of the anatomical feature of interest as closely as possible, in case of a sequence of 3D image data, preferably over the whole sequence of images. In particular, the MPR-view may occupy a smaller viewing area/e.g. 2 to 20%) as compared to the 3D rendering. That is, who is looking at the viewing area may see both the MPR-view and the 3D rendering simultaneously. For example, the 3D rendering is a representation of an anatomical structure, and the anatomical feature of interest is a part of said anatomical structure or adjacent thereto. As an example, the MPR-view covers less than ⅕ of the 3D rendering in the viewing direction of the user. As a result, the user may have the overview of the anatomical structure and is aware where exactly the MPR-view is positioned. Thus, a misplacement of the MPR-view prior to a measurement within the MPR-view may be prohibited.

The MPR-view may be based on the 3D medical image data and may thus always include all available information unrepented of any adjustment of the threshold of the 3D rendering or an adjustment of other parameters.

According to a useful embodiment, the input tool as described above allows a user to select a plane in the 3D rendering. The method then preferably comprises a step of displaying a multi planar reconstruction (MPR) of the selected plane of at least one of the three-dimensional medical images of the sequence, in particular at the position in the three-dimensional visualisation environment corresponding to the selected plane. Displaying a MPR-view in addition to the 3D rendering allows the user to view the anatomical structure in more detail. In the virtual reality environment, thanks to the 18 degrees of freedom (VR headset and two controllers), the correct positioning of a touchable/graspable MPR view in the 3D rendering is very fast and verifiable, and measurements on the MPR view or within the volume-rendered part (i.e. within the 3D rendering) become more precise and reliable.

The cropping body or clipping body may be a body having a volume, but being transparent such that a user can look through it. In other words, any voxels within the cropping body may be set to have a grey-scale value of zero. In another embodiment, all voxels within the cropping body can be excluded from the volume rendering and treated as non-existent. In this case, even with a threshold of 0, no 3D rendering can be present within the cropping body. The cropping body may be defined by a superficies surface surrounding the volume of the cropping body. That is, any part of the 3D rendering that is positioned within the volume, may be cropped (i.e. cut) away. The position of the cropping body may be determined in relation to the position of the 2D-frame. That is, wherever a 2D-frame is provided (refer to the above) a cropping body may be provided, too. Accordingly, the user may readily look at the 2D-frame (i.e. at the MPR-view depicted within the 2D-frame). If there is more than one 2D-frame in the visualisation environment, there may be the same number of cropping bodies in the visualisation environment. In other words, the cropping body may partly crop the 3D rendering between the first side of the 2D-frame and the user. That is, the cropping body may form a kind of tunnel through the 3D rendering to the 2D-frame. The user may look through said tunnel at the 2D-frame. This allows the user to easily view the MPR-view displayed in the 2D-frame and also see the 3D rendering around the 2D-frame. Further, the cropping body may adapt its size, shape and/or position to the position of the 2D-frame. For example, in case the 2D-frame is moved, the cropping body may move accordingly such that the user has still an unobstructed view at the 2D-frame. Accordingly, in case the 3D rendering is moved and/or rotated, the cropping body may adapt itself such that the user has an unobstructed view at the 2D-frame. That is, in case the 2D-frame is moved further into the 3D rendering, the cropping body may expand its size so as to partly crop away the 3D rendering at the first side such that the user has an unobstructed view at the 2D-frame. The cropping body may also adapt its size and shape to the size and shape, respectively, of the 2D-frame. Further, the 3D rendering and the cropping body may be instantly updated (e.g. 60-90 updates/second) based on a user's movement (i.e. changing of the view direction of the user) and/or on the size/shape/position of the 2D frame.

The invention is particularly useful for viewing and analysing a particular anatomical feature of interest, which is usually a part of the anatomical structure. Such feature of interest is in particular contained in a smaller volume of interest (VOI) than the complete field of view of the 3D rendering. It may be a part of the organ constituting the anatomical structure, in particular a part having a complex anatomy, such as a heart valve. In useful embodiments, the anatomical feature of interest is the mitral valve, the tricuspid valve, the aortic valve or the pulmonary valve. In other embodiments, the anatomical feature of interest may be the heart chambers or other important blood vessels such as the coronary blood vessel, or another structure such as a tumour.

In order to allow a user to view and analyse the anatomical feature of interest, the visualisation environment is provided for visualising at least two different kinds of visualisation/depictions. These are in the same coordinate system, i. e. they are displayed in the correct relative spatial positions and orientations with regard to one another. The at least two visualised objects are:

(i) A 3D rendering of the 3D medical image data. Thereby, the user is given a detailed and unobstructed view of the whole anatomical structure comprised in the 3D medical image data. In useful embodiments, the selected settings/parameters for the volume rendering, such as a threshold, smoothing etc., are either adjusted automatically and/or manually by a user.

(ii) Secondly, a MPR-view depicted within the 2D-frame. Thereby, the user is given further detailed information of the 3D medical image data at the specific position of the 2D-frame. For example, when analysing the mitral valve by inspecting the MPR-view within the 2D-frame, the user can at the same time keep track of the surrounding portions of the heart, e.g. the left ventricular outflow tract (LVOT). This is important when planning interventional procedures such as valve replacement, e.g. transcatheter aortic valve implantation (TAVI) or transcatheter aortic valve replacement (TAVR), or a replacement of the mitral valve, in which the LVOT may not be obstructed.

Preferably, the first side of the 2D-frame is facing the user so as to be at least substantially orthogonal to a viewing direction of the user. Substantially orthogonal may be considered as being oriented in an angle of between 80° to 100°, preferably between 88° to 92°, to the user's viewing direction i.e. the viewing direction of the 3D rendering. In this range the 2D-frame (and thus the MPR-view) is advantageously visible for the user. If, on the other hand, the 2D-frame were tilted at an angle outside the ranges defined above, the MPR-view displayed in the 2D-frame would not be visible correctly due to the inclination of the MPR-view. Furthermore, measurements made in such a tilted 2D-frame would be rather inaccurate. The first range defined above provides a sufficient visibility of the MPR-view in particular for a correct positioning of the 2D-frame within the 3D rendering. The second range provides an advantageous orientation of the MPR-view for accurate measurements. As described above, the 2D-frame always automatically orients itself to the user so as to be oriented in the above range, regardless of whether the user changes his or her viewing direction and/or the 2D-frame is moved. This simplifies the usability for the user, as he does not have to worry about a correct alignment of the 2D-frame, but can work as it is best for the analysis of the 3D rendering. In addition, the user may issue a command such that a predefined view is depicted by the MPR-view. In other words, upon receiving such command, the 3D rendering may be automatically rotated such that the predefined view is depicted by the MPR-view within the 2D-frame. Such predefined view may be a parasternal long axis view, a parasternal short axis (i.e. a rotation of the 3D rendering by 90° with respect to the parasternal long axis view), a two-chamber view, a three-chamber view, and/or a four-chamber view.

According to an embodiment, the cropping body is positioned directly adjacent to the 2D-frame so as to crop the 3D rendering between the first side of the 2D-frame and the user. In this case any part of the 3D rendering that is positioned between the 2D-frame and the user may be cut away (cropped). Accordingly, the entire MPR-view is visible to the user. In other words, no part of the 3D rendering interferes with the direct viewing of the entire MPR-view within the 2D-frame. This is particularly useful when the MPR-view is to be analysed in great detail. For example, measurements or other analysis methods can easily be carried out in the MPR-view. Such operations can thus not be hindered by parts of the 3D rendering between the first side of the 2D-frame and the user.

According to an alternative embodiment, the cropping body may not be directly adjacent to the 2D-frame and a ratio between the shortest distance of the cropping body to the 2D-frame and the length of the perimeter of the 2D-frame is between 0.1 to 0.9, preferably between 0.1 and 0.6 and most preferably between 0.1 and 0.4. In other words, the cropping body does not extend to the 2D-frame, so it is not directly adjacent to the 2D-frame. That is, a part of the 3D rendering may be positioned between the first side of the 2D-frame and the user. For example, part of the 3D rendering may extend through the MPR-view. For simplicity, the MPR-view can be thought of as a base from which part of the 3D rendering is erected to the beginning of the cropping body. The extent of such an erection can be defined by the distance between the 2D-frame and the cropping body. In this case the user may view the MPR-view and a part of the 3D rendering at the position of the MPR-view. The ranges defined above define an extension of the 3D rendering towards the user from the first side of the 2D-frame in relation to the perimeter of the 2D-frame. In other words, the larger the perimeter, the larger the extension of the 3D rendering on the first side. This is useful because if the user creates a large 2D-frame, the user will also see a larger part of the 3D representation than in the case where the user creates a rather small 2D-frame. As a result, the extension of the 3D rendering may adapt itself to the size of the 2D-frame set by the user.

The range from 0.1 to 0.9 is particularly useful for positioning the 2D-frame. Since part of the 3D rendering extends through the MPR-view, the user may easily orientate himself to place the 2D-frame correctly in the visualisation environment. Since the MPR-view is opaque, the visibility of a part of the 3D rendering on the first side of the 2D-frame helps the user to know what is behind the 2D-frame (i.e. at the second side of the 2D-frame). Consequently, fewer back and forth movements of the 2D-frame are necessary in order to position the 2D-frame correctly.

In addition, the range of 0.1 to 0.6 is particularly useful for checking whether an additional model provided fits the anatomical structure. The model may be a surface model representing a medical instrument such as an artificial heart valve, pacemaker or other instrument intended for insertion into the human or animal body. The model may have handles that allow the user to adapt the model or parts of the model to the anatomical structure. It may be helpful for the 3D rendering to be partially visible on the first side of the 2D-frame.

The range of 0.1 to 0.4 is particularly useful for calibrating the threshold of the 3D rendering to the 3D medical image data. It is to be noted that the visualisation of the 3D rendering is dependent on the threshold setting. Therefore, the MPR-view may be used to calibrate the 3D rendering to find the threshold setting that best fits the 3D medical image data. In the range above, there is only a small extension of the 3D rendering through the MPR-view. This allows the user to adjust the 3D rendering that builds from the first side of the 2D-frame to the contour represented by the MPR-view. That is, the threshold of the 3D rendering can be varied until the 3D rendering rising from the first side of the 2D-frame is aligned with a contour of the anatomical structure depicted on the MPR-view. Accordingly, the threshold can be easily set which represents the 3D medical image data best. According to another embodiment, the distance between the cropping body and the 2D frame may be variably adjusted. Accordingly, each user may individually adjust how much of the 3D rendering extends on the first side of the 2D-frame.

The method further comprises receiving a user's command so as to change the size of the 2D-frame in the visualisation environment, wherein the MPR-view within the 2D-frame is updated to the new size of the 2D-frame, and wherein the size of the transparent cropping body is adapted to the new size of the 2D-frame.

Preferably, the method further comprises receiving a user's command so as to change the position of the 2D-frame in the visualisation environment, wherein the MPR-view within the 2D-frame is updated to the new position of the 2D-frame, and wherein the position of the transparent cropping body is adapted to the new position of the 2D-frame. The user's command may be similar to the above-described commands for providing the 2D-frame within the visualisation environment. For example, the 2D-frame may have a virtual handle at which it may be grasped and moved through the visualisation environment. Further, the user may enter coordinates at which the 2D-frame should be positioned. Such entering may be realized by using a keyboard or any other input medium. In addition, the 2D image may be rotated and/or enlarged or reduced. The MPR-view depicted within the 2D-frame may be automatically updated based on the new position and/or size of the 2D-frame relative to the 3D medical image data. The updated MPR-view may be still based on the 3D medical image data. Therefore, a transfer of inaccuracies of the 3D rendering into the MPR-view may be avoided. That is, the at least one 2D-frame may have a fixed orientation facing the user, independent of the user's viewing direction, and wherein the MPR-view within the 2D-frame may be automatically updated as the 3D rendering is moved relative to the 2D-frame or vice versa.

Preferably, the 2D-frame is provided in an analysing plane extending in two dimensions through the 3D rendering, wherein the 2D-frame covers only a part of the analysing plane. The analysis plane may be transparent so that the user's view is not obstructed by the analysis plane. The 2D-frame can be on top of the analysis plane or may be parallel to the analysing plane. Since the 2D-frame only covers part of the 3D rendering, the 2D-frame can be smaller than the analysis plane.

According to an embodiment, the transparent cropping body has an adaptable cross-section and the method further comprises the step of receiving a user's command indicative of a ratio in which the size of the cross-section changes with increasing distance from the 2D-frame. As described above, the cropping body may define a volume that extends between the 2D-frame and the user. Wherever the volume of the cropping body exists, the 3D rendering is cropped away. Further, the cropping body may additionally crop any element displayed within the visualisation environment between the 2D-frame and the user such as surface models etc. Since the cropping body is transparent, the user can see through it to see the 2D-frame and thus the MPR-view displayed in the 2D-frame. The cropping body may be defined by a plurality of cross sections that are stacked onto each other so as to form the cropping body, wherein each cross section is parallel to the 2D-frame. In one embodiment the cropping body has constant cross sections, that is, each cross section has the same dimension. In other words, the cropping body may have a cylindrical shape. In another embodiment, the cross sections may have different dimensions. In this way, differently shaped cropping bodies may be achieved by varying the cross-section. According to an embodiment of the present invention, the cross sections may be adaptable so as to vary the shape of the cropping body during executing the examination. That is, the user may issue a command so as to change the shape and/or dimension of the cropping body. As an initial setup all cross sections of the cropping body may have the same dimensions. In this case, the distal cross section closest to the 2D-frame and a proximal cross section closest to the viewing position of the user may have the same dimensions. However, any other arrangement of cross sections may be set as the initial setup. For example, the cutting body may have a funnel shape. That is, the distal cross-section may be the smallest cross-section and each cross-section towards the proximal cross-section may be larger than the previous one. This is also possible the other way around, with the proximal cross-section being the smallest. Therefore, the cropping body may be adapted to the user's preferences and to the kind of examination that is carried out. For example, for the purpose of spatial orientation, it may be advantageous to have a cropping body that is as small as possible (so as to see as much as possible of the 3D rendering, but also the MPR-view).

Further, the distal cross section may have the same shape and dimension as the 2D-frame. Accordingly, it may be ensured that the 2D-frame is readily visible for the user through the cropping body. Furthermore, the cropping body may be changed in its shape and then returned to its initial position. The change of the cropping body may be animated so that the cropping body continuously changes its shape and then continuously returns to its initial position, for example. Accordingly, the user may get a very good spatial impression of the entire anatomical structure. In addition, the cropping body may continuously expand its size until everything is cropped away from the 3D rendering on the first side of the 2D-frame. In this case, the user may face the entire surface of the analysis plane. This is advantageous for taking measurements or obtaining a 2D view of the anatomical structure.

Preferably, the method further includes:

receiving a user's command so as to rotate and/or move the 3D rendering such that the 3D rendering has a new position and/or orientation within the visualisation environment, wherein the MPR-view within the 2D-frame is updated in correspondence to the new position of the 3D rendering, and/or wherein the shape and/or size of the cropping body is updated in correspondence to the new position of the 3D rendering. That is, the 3D rendering may be moved and/or rotated by the user. This may be necessary for inspecting a feature of the anatomical structure at the rear of the anatomical structure. Further, moving the 3D rendering may improve the 3D recognition of the user. As described above the 2D-frame may be provided within the visualisation environment according to one of options I) to IV) (refer to the above outlined). In the case where the 2D-frame is not fixed to the 3D rendering (as in case II)), the 2D-frame may remain at its position while the 3D rendering is moved and/or rotated. However, the MPR-view within the 2D-frame may be updated as the 3D rendering is moved and/or rotated with respect to the 2D-frame. Similarly, the cropping body may be updated, too. That is, due to moving and/or rotating the 3D rendering, there may be a bigger portion of the 3D rendering at the first side (i.e. between the user and the 2D-frame) that has to be cut away so as to provide a visibility of the MPR-view. Accordingly, the cropping body may be adapted in its shape and/or dimension so as to crop the bigger portion of the 3D rendering at the first side of the 2D-frame away. As a result, a smooth workflow may be attained in which the user has always a good view to the MPR-view independent of the position of the 3D rendering relative to the 2D-frame. In addition, the MPR-view may be always updated based on the 3D medical images (i.e. based in the ground truth).

Preferably, the method further comprising:

receiving a user's command indicative of a second point on or within the 3D rendering;

providing a second 2D-frame at a position in the visualisation environment in correspondence to the second point, wherein a first side of the second 2D-frame is facing the user, wherein the second 2D-frame is preferably at least substantially orthogonal to a viewing direction of the user, displaying a second MPR-view within the second 2D-frame, wherein the second MPR-view is based on the 3D medical image data at the position of the second 2D-frame and is sized so as to correspond to the size of the second 2D-frame; and providing a second transparent cropping body between the user and the first side of the second 2D-frame so as to partly crop the 3D rendering. The second 2D-frame and/or the second cropping body may have the same properties as the first 2D-frame and the first cropping body described above. This holds also true for issuing of the second 2D-frame and or the second cropping body. Furthermore, there may be further 2D-frames added to the visualisation environment. For example, three, four, five and six 2D-frames may be provided.

The further 2D-frame may be useful for analysing and comparing two small features of the anatomical structure that are spaced apart. In this case, the overview of the anatomical structure may be ensured while at the same time the features may be examined in great detail.

Preferably, the method further comprising the step of receiving a user's command so as to individually change the shape and/or size of the at least one 2D-frame. That is, each 2D-frame may be individually adapted (i.e. the shape and/or size of the 2D-frame may be changed). Hence, the 2D-frame may be adapted to the Size of the respective feature under examination. For example, the shape of the cross-section can be changed from circular to polygonal and vice versa. Furthermore, there may be provided a third, fourth and fifth frame. In other words, a plurality of 2D-frames may be provided that may have the same characteristics as the first 2D-frame and/or may be provided similarly to the first 2D-frame.

Preferably, the method further comprising the step of receiving a user's command indicative of a measuring along a measuring path beginning at the first point set by the user, wherein the 2D-frame surrounds the first point and the measuring path, and adapts its size and/or shape dynamically to the measuring path, and receiving a user's command indicative of a position at which the measuring path ends. Accordingly, the user may enter into a measuring mode. In this mode, the user may issue the command indicative of the first point so as to provide the first 2D-frame. The measurement may be started at the first point. Then, the user may indicate a second point to which a distance should be measured. In this way a diameter of a heart valve or a vessel may be measured. For example, the user may press a button on the pointing device to indicate the position of the first point. Then the user can move the pointing device to the second point while holding down the button. Upon reaching the second point, the user can release the button to indicate the position of the second point.

Further, the 2D-frame may be provided at the first position as described above. In addition, the 2D-frame may stretch itself to the second point so as to cover the measuring path. As a result, a 2D-frame is created after the measurement, covering the first and second points and the space between the first and second points. In this case the user may look at the MPR-view within the 2D-frame so as to better find the second point (e.g. a boundary of a vessel or a cavity). Consequently, the quality of the measurement may be improved.

If a single point is set, the 2D-frame defined by this point can still rotate around all three rotational degrees of freedom (roll, pitch, yaw). As soon as a second point is defined for the 2D-frame, two of these degrees of freedom are dropped and the 2D-frame region can only rotate around one axis. If a third point is set, the 2D-frame is rigid and has no more degrees of freedom. That is, only the transparent cropping body may adjust itselfs to a rotating and/or moving 3D rendering or to a changed viewing position of the user to allow a free view of this rigid 2D-frame (i.e. at the MPR-view) at any time.

Alternatively, two 2D-frames may be provided one at the first point (start of the measurement) and one at the second point (target of the measurement). In this case, in between the two points the 3D rendering is still visible. Therefore, the user may have a good spatial understanding of the space between the points. If two points are set by the user, the shortest distance between these two points can be measured automatically in each case. The first point that may be used to provide the 2D-frame for that point may be the same first point that may be used as the starting point for a measurement. Alternatively, these points may be separate points to be specified separately by the user. Preferably, the visualisation environment is a VR-environment or an AR-environment. According to a useful embodiment, the three-dimensional visualisation environment is a virtual reality environment. By "virtual reality", any computer-generated visualisation providing a truly three-dimensional experience of the depicted structure is meant. Accordingly, the virtual reality (VR) environment of the invention provides in particular visual feedback, but may also allow other types of sensory feedback, such as auditory. The VR environment may also be an augmented reality environment, wherein the user stills sees the real environment, but with the VR objects (e.g. the volume rendering and the dynamic model) overlaid or superimposed on the reality objects, or a mixed reality, in which real-world objects are superimposed on a virtual scene. Together, the volume-rendered VOI and the visualisation of the dynamic model may form a visualised object, preferably a virtual reality object.

The virtual reality environment is generally realised by presenting stereo images to the user, i.e. each eye sees a different image, so that the brain will put together the two different images to a true three-dimensional scene. Such binocular images may be presented on any VR display, such as a virtual reality headset or a multi-projected environment, or a screen showing the two images intermittently, in connection with shutter glasses.

In the VR environment, the volume rendered VOI and the dynamic model may be displayed by stereoscopic rendering: Therein, the volume rendered (or otherwise rendered) visualisation/image is calculated twice, for two viewing positions having a slight spatial offset, i.e. one viewing position for the left eye and one for the right eye. When the two thus calculated visualisations are shown to the user one on each eye, e.g. on a VR headset, the user gains a truly three-dimensional (VR) impression. Thereby, the volume rendered VOI and the dynamic surface model can be converted, viewed and analysed in VR.

In a preferred embodiment, a person using an inventive VR environment is able to "look around" the artificial world, move around in it, and interact with virtual objects, features or items. The effect is commonly created by VR headsets comprising a head-mounted display with a small screen in front of each eye, but can also be created through specially designed rooms with multiple large screens. In order for the user to move around in the VR environment, position and orientation information have to be transmitted by the headset to the electronic device (e. g. computer or a processing unit within the head set) generating the VR environment, so that the visualisation is moving in coherence with head movements of the user. In order for the user to interact with virtual features in the VR environment, also hand movements must be tracked, which may be done by hand-held VR controllers. However, this last feature is optional, as well as the transmission of position/orientation information in order for the user to walk around in the virtual scene.

The virtual reality environment provides the advantage that the user may view and analyse the visualised object with great confidence, since he obtains a truly three-dimensional view of the anatomical structure. Further, since he can walk around it and possibly even into it, he can have the visualised object (e. g. the visualisation of the human heart) displayed in huge magnification, so as to completely fill the space in front of the user. Therefore, the user has a particularly good overview and may take measurements with great accuracy. Further, the handling of user input events is particularly easy and intuitive in a VR environment. Actions such as rotating the objects and/or adjusting the settings of the volume-rendered VOI, which may be quite tricky on a two-dimensional screen, are very intuitive and fast in a VR environment using VR controllers.

However, the invention may also be advantageously used with non-VR visualisation environments. Where VR (virtual reality) is not specifically mentioned, the features and embodiments described herein are useful for both VR and non-VR visualisation environments.

Preferably, the method further comprises the step of receiving a user's command so as to provide a cropping plane extending through the whole 3D rendering and cropping the 3D rendering at one side of the cropping plane, wherein the cropping plane has an individual orientation and position within the visualisation environment. At one side of the cropping plane, at least the 3D rendering may be cropped away. In addition, any other model or visualisation within the visualisation environment may be cut away at one side of the cropping plane. In other words, the cropping plane can represent a 2D boundary within the visualisation environment, on one side of which objects such as the 3D rendering are mapped, while on the other side at least the 3D rendering is cropped or clipped away. The cropping plane may have an extension in two dimensions throughout the visualisation environment. Accordingly, it is ensured that every part of the 3D rendering is cut away even if the boundary of the 3D rendering is not exactly determined. Alternatively, the cropping plane may extend only throughout the 3D rendering. This ensures that the other visualisations within the visualisation environment are still visible for the user. The cropping plane may be freely moved based on a user's command. That is, in contrast to the 2D-frame which is facing the user, the cropping plane may be freely positioned and/or oriented within the visualisation environment. For example, the user may look at the 3D rendering in a first direction and may partly crop away the 3D rendering in a second direction being orthogonal to the first direction. As a result, the user may reduce the 3D rendering to an efficient size necessary for his examination. This further simplifies the examination and ensures a clear visualisation of the important part of the 3D medical image data.

Preferably, the method further includes the step of automatically segmenting a surface model from the 3D medical image data, wherein the surface model corresponds to at least a part of the anatomical structure;

displaying the surface model within the visualisation environment, and receiving a user's command so as to adjust the surface model to the MPR-view within the 2D-frame. For example, surface models may be automatically segmented from 3D medical image data. That is, based on 3D medical image data a ventricle of a heart may be at least partly represented by a surface model. The surface models can then be used for further examinations or planning operations. Therefore, it is preferable that the surface models represent the 3D medical image data as best as possible. One way the check whether the surface model fits to the 3D medical image data is to compare the surface model with the 3D rendering. However, due to the rendering process according to which the 3D rendering depends on which threshold is set, there may be inaccuracies in the 3D rendering. On the other hand, using MPR-views alone may be complicated because the spatial orientation is not easy for a user. According to the present embodiment, the surface model may be checked by using both the 3D rendering and the MPR-view (depicted within the 2D-frame). For example, the user may issue a command so as to display the surface model in addition to the 3D rendering and the 2D-frame within the visualisation environment. Then the user may position the 2D-frame such that the MPR-view lies at least partly on the surface model. Consequently, the user may check whether the surface model corresponds to the respective feature (e.g. to a boundary) depicted by the MPR-view. Since the 3D rendering is visible around the 2D-frame, the user may easily orient himself Hence, the surface model may be checked in an efficient and accurate manner. According to another embodiment, the user can adjust the surface model to perfectly match the 3D medical image data. For example, the user can move or adjust the surface model to match the 3D medical image data. In this context, for example, control points defining the shape and size of the surface model can be moved.

According to another aspect, the invention provides a computer program comprising program code instructions which, when executed by a processor, enables the processor to carry out the inventive method. The computer program may be in any code, in particular a code suited for computer graphic applications, in particular for VR programming.

In a further aspect, the invention is directed to a computer-readable medium comprising an above-defined computer program. The computer-readable medium may be any digital data storage device, such as a USB-stick, hard disk, CD-ROM, SD card or SSD card. Naturally, the computer program need not be stored on such a computer-readable medium to be supplied the customers, but may be downloadable via the internet.

According to another aspect, the invention provides an 3D medical image data evaluation device configured to perform the inventive method, the evaluation device comprising:

- an interface for receiving 3D medical image data,
- a computing unit for performing the inventive method, and
- a visualisation device for providing the visualisation environment and for displaying at least the 3D rendering and the 2D-frame.

All embodiments described herein are applicable both for "conventional" visualisation environment that can be realised on computer screen, tablet computer or display, as well as in a VR environment. However, the VR environment is particularly advantageous because it provides a true 3D view and the most intuitive/fast user experience/handling as well as 6, 12 or 18 degrees of freedom in which the user can move with respect to the visualised object.

Preferably, the method according to the invention is executed by a processor which may be incorporated in any electronic device able to control a display, in particular a VR display such as a VR headset or projection display. Such digital device may be a computer, PC, server, television set, tablet computer, smartphone, laptop, hand-held device or the like. The processor may also be part of a cloud computer, workstation, or the control console of a medical image device, in particular an ultrasound scanner.

Individual features of the embodiments described above may be combined with other embodiments or with other features of other embodiments to form new embodiments. The effect mentioned in connection with each individual feature also applies to such new embodiments. Furthermore, the advantages and configurations mentioned in connection with the method also apply to the device and vice versa.

SHORT DESCRIPTION OF THE FIGURES

Useful embodiments of the invention shall now be described with reference to the attached figures. Similar elements or features are designated with the same reference signs in the figures. In the figures.

DESCRIPTION OF EMBODIMENTS

Figure 1:
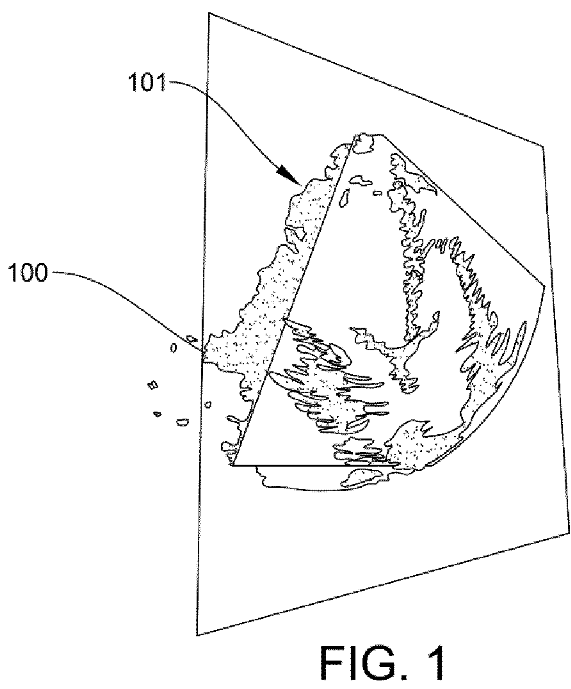
FIG. 1 shows a schematic visualisation of the prior art.

FIG. 1 shows a state-of-the-art visualisation method. In particular, in FIG. 1 there is shown a 3D rendering 101 and a MPR-view 100 which extends through the 3D rendering 101. In front of the MPR-view 100 no 3D rendering is visible for the user looking at the MPR-view 100. Behind the MPR-view 100 the 3D rendering is not visible, too, due to the obliged MPR-view 100. Accordingly, the user can hardly orient himself using the 3D rendering 101.

Figure 2:
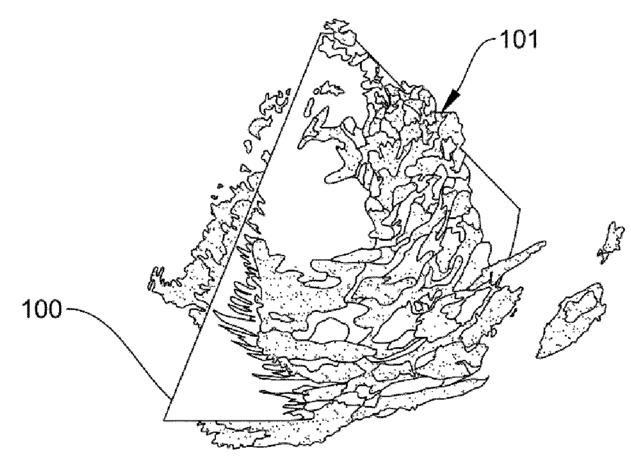
FIG. 2 shows a schematic visualisation of the prior art.

FIG. 2. also shows a state-of-the-art visualisation method. In this case, the 3D rendering 100 is not cut away in front of the MPR-view 100. However, the 3D rendering 101 blocks a clear view of the MPR-view 100. In this case, the user can orientate himself on the 3D rendering 101, but can hardly see the MPR-view 100.

Figure 3:
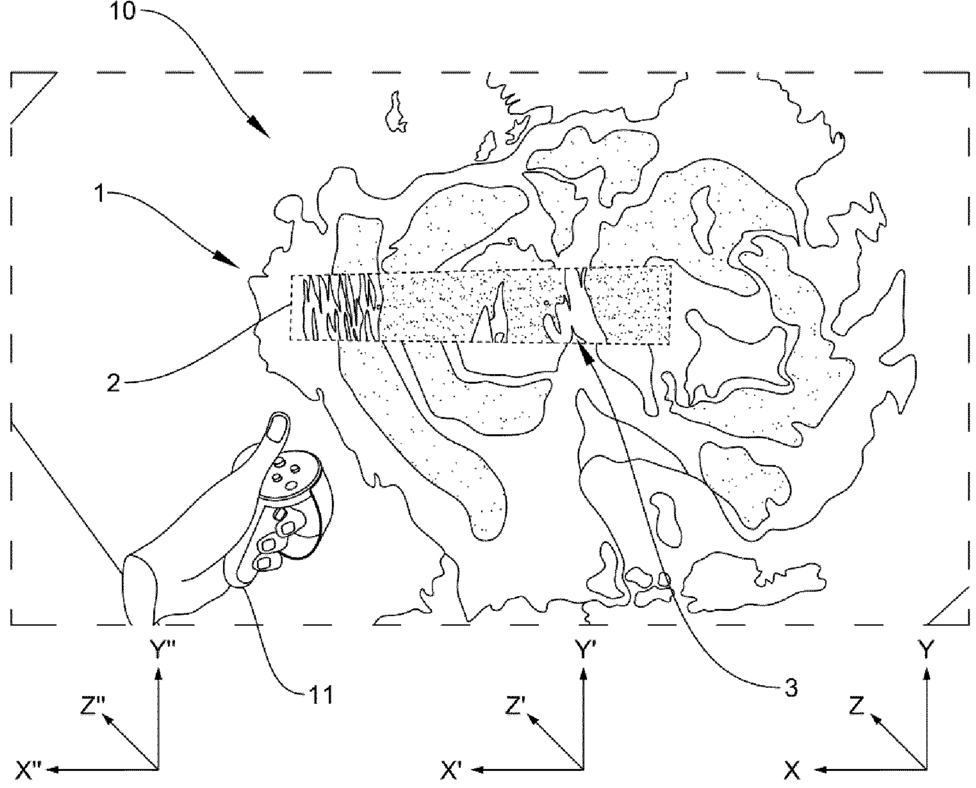
FIG. 3 shows a schematic representation of depicting a 3D rendering and a MPR-view according to an embodiment of the present invention.

FIG. 3 shows a visualisation method according to an embodiment of the present invention. In particular, in FIG. 3 there is depicted a 3D rendering 1 in a visualisation environment 10. Within the visualisation environment 10 a 2D-frame 2 is provided in which a MPR-view 3 is depicted. FIG. 3 corresponds to a view of the user. The 2D-frame 2 is provided such that it faces the user. In other words, the 2D-frame 2 is arranged and oriented within the visualisation environment such that the user may always see the MPR-view 3 within the 2D-frame 2. The 2D-frame 2 and/or the 3D rendering 1 may be moved and/or rotated relative to each other. Nevertheless, the 2D-frame 2 automatically orients itself such RECTIFIED SHEET (RULE 91) ISA/EP that it is facing the user. In addition, the user may change his viewing direction and even in this case the 2D-frame 2 orients itself such that it is facing the user and the user may see the MPR-view 3. Furthermore, any time the 2D-frame 2 changes its position relative to the 3D rendering 1, the MPR-view 3 depicted within the 2D-frame 2 is updated based on the new relative position. It is to be noted that the MPR-view is determined based on 3D medical image data and represents thus the ground truth of the 3D medical image data. In the present embodiment the visualisation environment 10 is a VR environment and the user controls the method by using at least one controller 11. Further, in the present embodiment the 2D-frame 2 has a rectangular shape. However, the 2D-frame 2 can also have any other shape that is most suitable for the examination to be carried out.

Moreover, by grasping the 2D-frame 2, the user may adjust the size of the 2D-frame 2. That is, the 2D-frame 2 may be enlarged and reduced in accordance to the preferences of the user. In order to always have an unobstructed view of the MPR-view 3, there is provided a cropping body 8 (refer to FIG. 7) which at least partly crops the 3D rendering away at a first side of the 2D-frame 2. As a result, the user may see the MPR-view 3 regardless how deep the 2D-frame 2 is moved into the 3D rendering 1. In addition, in FIG. 3 there are shown three coordinate systems. The visualisation coordinate system defining the coordinates X, Y and Z in which the viewing position of the user and the controller 11 of the user is defined. Then, the object coordinate system X', Y' and Z' is defined in which the 3D rendering 1 and the 2D-frame 2 is defined. Lastly, the original coordinate system X", Y" and Z" is provided in which the 3D medical image data are defined. In the present embodiment the coordinate systems may be rotated and/or moved with respect to each other. For simplification of explanation, in the further figures the coordinate systems are not depicted, but also present.

Figure 4:
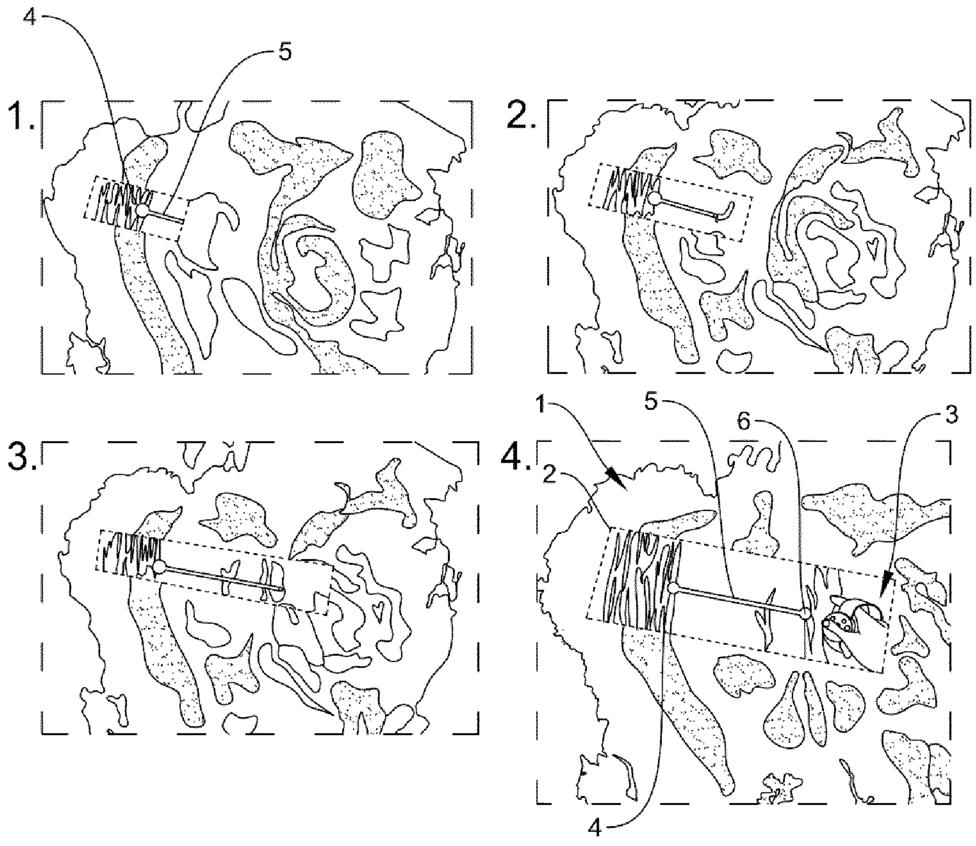
FIG. 4 shows a schematic representation of a measuring process according to an embodiment of the present invention.

FIG. 4 shows four subfigures showing a visualisation method according to another embodiment of the present invention. Specifically, in FIG. 4.1 the first point 4 set by the user is also a starting point for a measurement. That is, the first point 4 is the starting point for a measuring path 5. In addition, the 2D-frame 2 is provided within the visualisation environment 10 so as to depict the first point 4 in the MPR-view 3. Then the user may extend the measuring path 5 (refer to FIG. 4.2). The 2D-frame 2 and thus the MPR-view 3 is adapted in accordance to the extension of the measuring path 5. Then, in FIG. 4.3 the border of the vessel to be measured is visible within the MPR-view 3. Therefore, the user may accurately provide a second point 6 on the border. Thus, the measuring path extend between the first point 4 and the second point 6. In FIG. 4.4 the completed measuring path 5 is depicted by the MPR-view 3. The user then may individually adjust the 2D-frame 2. For example, the user may enlarge or reduce the 2D-frame so as to get a better impression of the neighbourhood of the measuring path 5.

Figure 5:
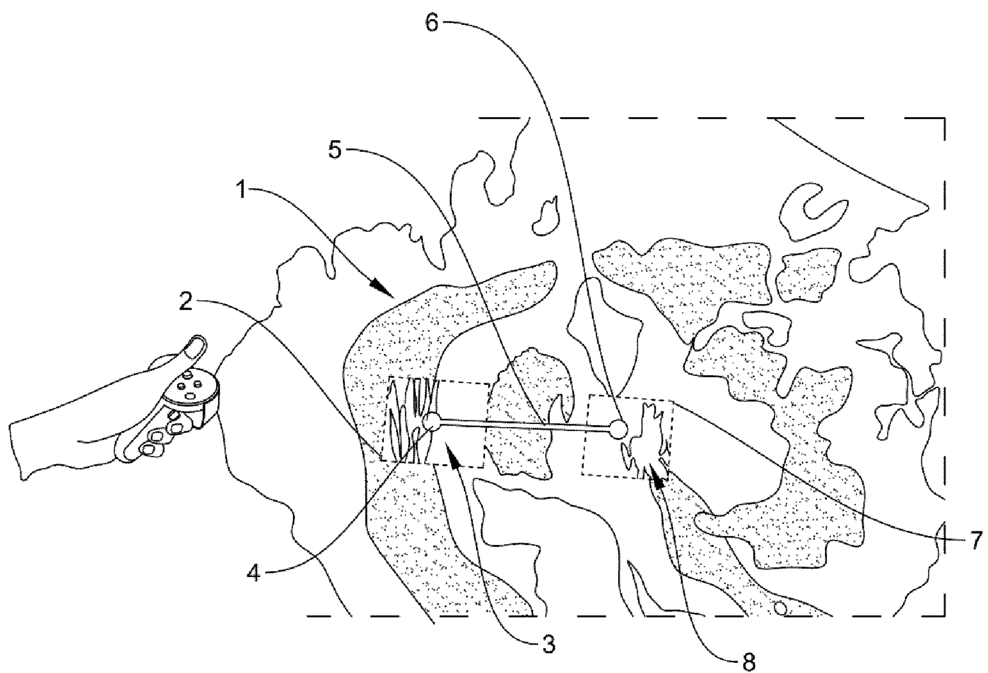
FIG. 5 shows a schematic representation of a measuring process according to another embodiment of the present invention.

FIG. 5 shows a visualisation method according to another embodiment of the present invention. The method of FIG. 5 differs from the method of FIG. 4 in that the 2D-frame 2 is not extended along the measuring path, but there are a first 2D-frame 2 provided at the first point 4 and a second 2D-frame 7 provided at the second point 6. The first 2D-frame 2 depicts the first MPR-view 3 and the second 2D-frame 7 depicts a second MPR-view 8. The measuring path 5 thus extends through the 3D rendering 1. In this case, the user may still accurately set the first and the second point due to seeing these positions within the first 2D-frame 2 and the second 2D-frame 7, but also have an increased impression of the spatial extension of the 3D rendering 1 because the user sees the spatial extension of the 3D rendering 1 between the first point 4 and the second point 6. It is to be noted that the second 2D-frame 7 has the same properties as the first 2D-frame. In addition, the second point 6 may be issued by the user in the same way as the first point 4.

Figure 6:
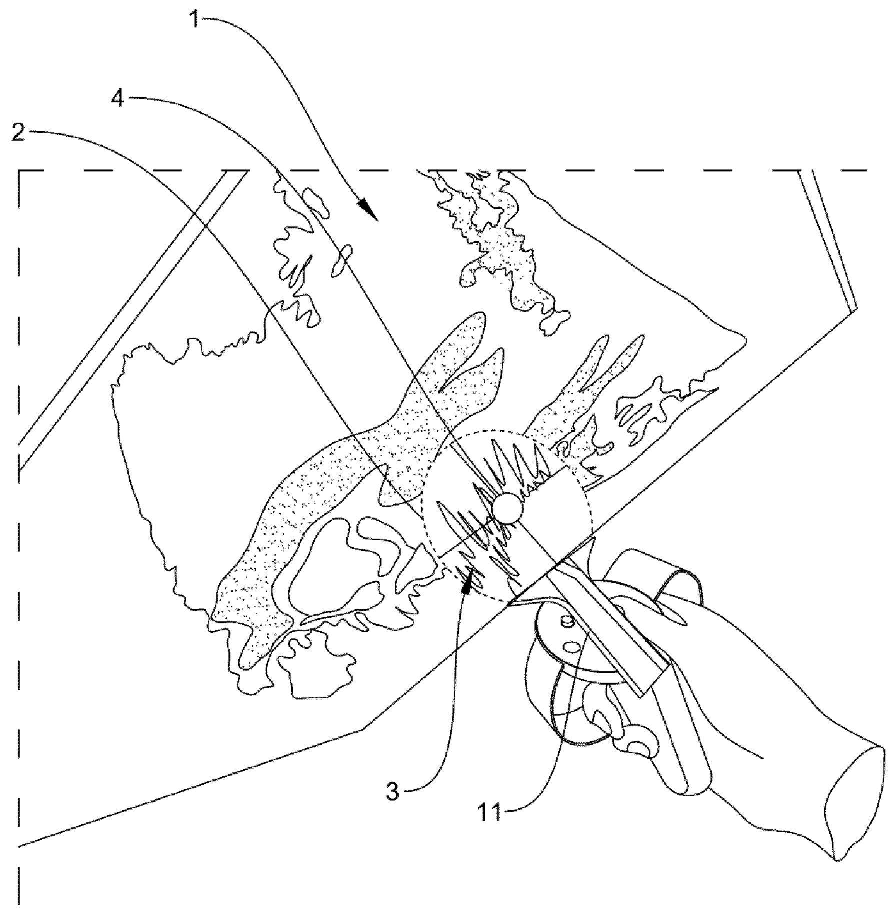
FIG. 6 shows a schematic representation of an analysing process according to an embodiment of the present invention.

FIG. 6 shows a further analysing method according to an embodiment of the present invention. As above in the present embodiment the visualisation environment is a VR environment. The user controls his commands using the controller 11. In the present embodiment, the user enters an analysing mode in which a 2D-frame is provided within the visualisation environment. For simplification of explanation the 2D-frame 2 may be considered a s a table tennis racket. In other words, the 2D-frame 2 has a handle at which the user may virtually grasp the 2D-frame 2. Accordingly, the 2D-frame 2 may be fixed to the controller 11 such that the 2D-frame 2 may be easily moved and/or rotated by simply moving the controller 11. In this way the user may virtually move the controller 11 through the 3D rendering 1 and may search for a specific feature, for example. As above, the MPR-view 3 is depicted within the 2D-frame 2 and is automatically adapted to the respective position of the 2D-frame 2 with respect to the 3D rendering 1.

Figure 7:
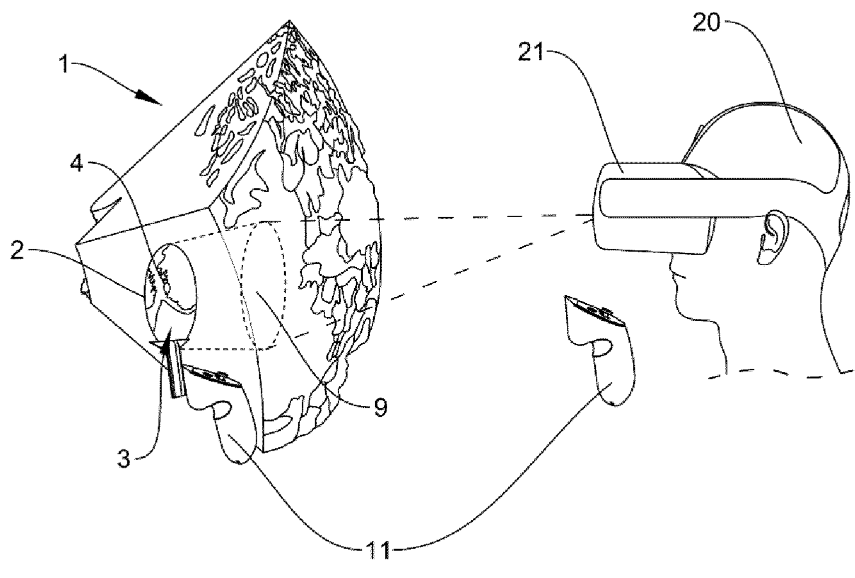
FIG. 7 shows a schematic representation of an analysing process according to another embodiment of the present invention.

FIG. 7 shows a schematic representation of an analysing process according to another embodiment of the present invention. The method of FIG. 7 substantially corresponds to the method depicted in FIG. 3. In FIG. 7, the scene is depicted in a sideview. Accordingly, the cropping body 9 may be seen. The cropping body 9 is provided at the first side of the 2D-frame 2 so as to cut away the 3D rendering. Therefore, the user 20 may have an unobstructed view of the MPR-view 3 within the 2D-frame 2. In addition, in this embodiment the 2D-frame 2 is virtually fixed to the controller 11 of the user 20 as described above in connection with FIG. 6. As above, the 2D-frame is moved through the 3D rendering 1 in order to find a feature and to position the first measuring point 4. The cropping body has an adaptable shape. That is, the cross sections orthogonal to the viewing direction of the user 20 and defining the cropping body 9 may have an individual shape and size. In the present embodiment, the cropping body 9 is sized and shaped such that the user has an unobstructed view of the MPR-view 3 within the 2D-frame 2. That is, the cropping body adapts itself to a new position of the 2D-frame 2 with respect to the 3D rendering 1. In summary, both the cropping body 9 and the MPR-view 3 adjust to a new position of the 2D-frame 2 to ensure the visibility of the MPR-view 3 to the user 20.

Figure 8:
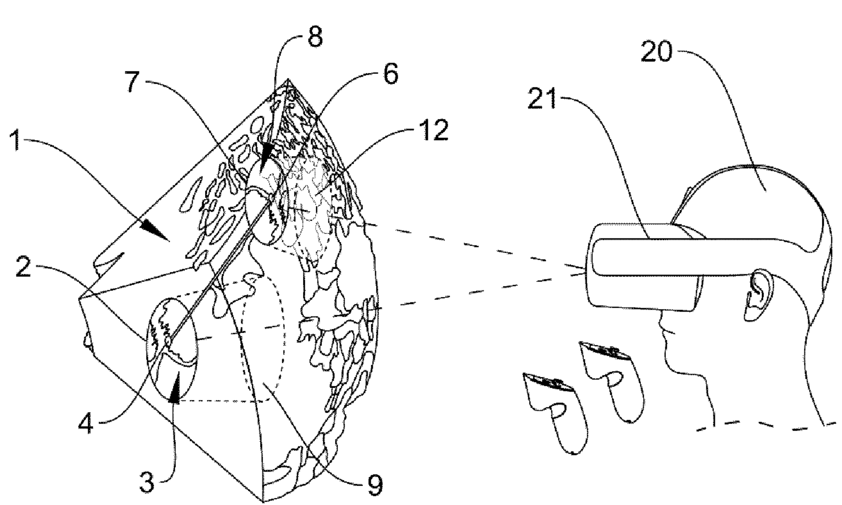
FIG. 8 shows a schematic representation of an analysing process according to another embodiment of the present invention.

FIG. 8 essentially corresponds to FIG. 7 with the difference that the second 2D-frame 7 depicting the second MPR-view 8 is provided. Accordingly, a second cropping body 12 is also provided at the first side of the second 2D-frame 7. As above, each 2D-frame 2, 7 is oriented so as to face the user. Accordingly, each cropping body 9, 12 is also oriented (i.e. sized and shaped) so as to be oriented to the user 20. In other words, each cropping body is provided such that the user 20 may have an unobstructed view of the respective MPR-views 3, 8. Therefore, the cropping bodies 9, 12 may have a different size and shape in case the two 2D-frame 2, 7 a positioned at different spatial positioned within the visualisation environment.

Figure 9:
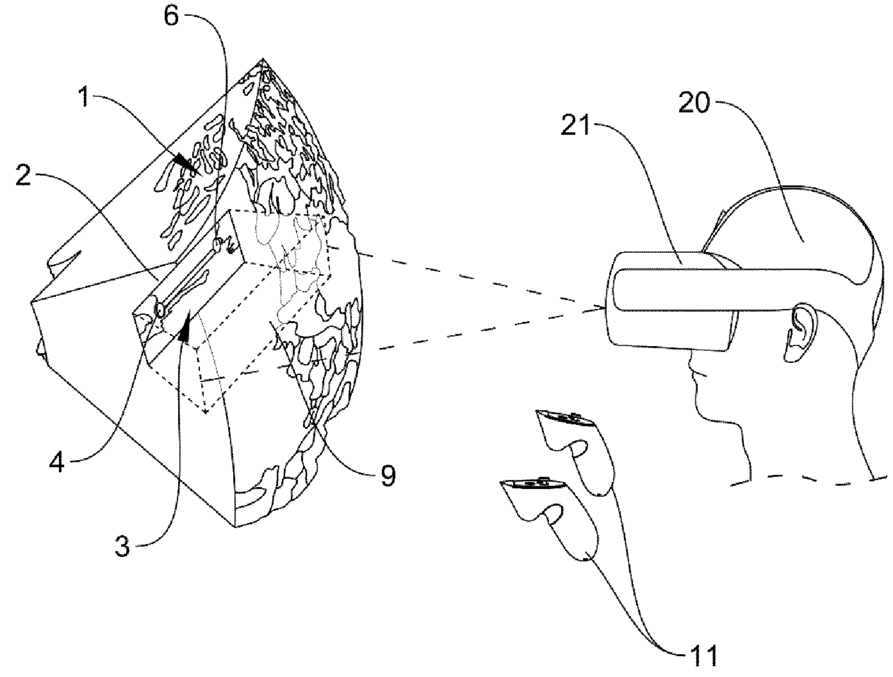
FIG. 9 shows a schematic representation of an analysing process according to another embodiment of the present invention.

FIG. 9 essentially corresponds to FIG. 7 with the difference that the 2D-frame 2 has another shape as in the embodiment of FIG. 3. In addition, the cropping body 9 has a tapered shape, wherein the cross section of the cropping body 9 that is closest to the user 20 has a bigger size as compared to the cross section of the cropping body 9 being closest to the 2D-frame 2. According, the user 20 may see the 3D rendering 1 at the walls of the cropping body 9. This may provide further information for the skilled person to better understand the anatomical structure depicted by the 3D rendering.

Figure 10A:
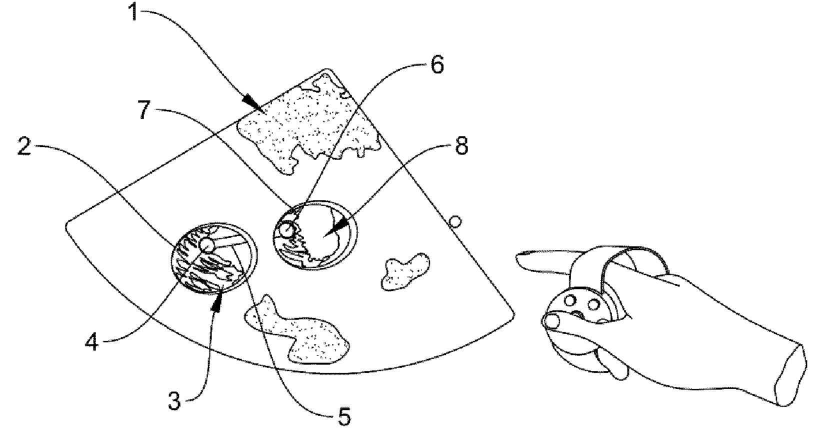
FIGS. 10A and 10B show a schematic representation of a 3D rendering with different thresholds and an analysing process according to an embodiment of the present invention.
Figure 10B:
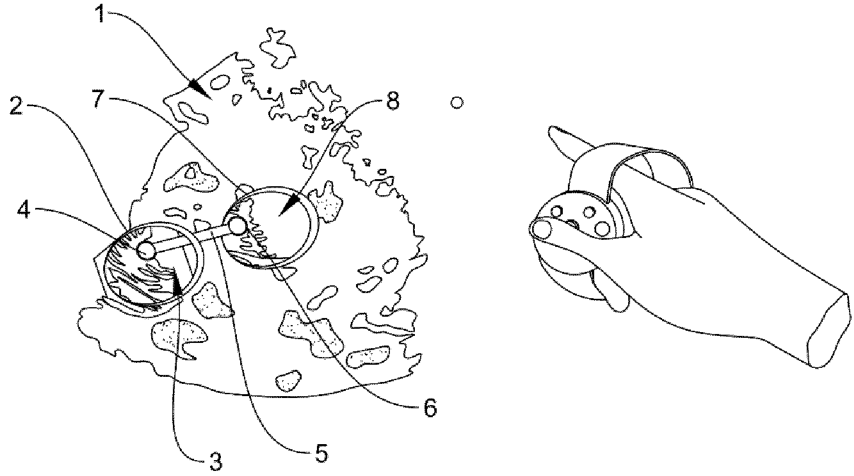

FIGS. 10A and 10B show a schematic representation of a 3D rendering 1 with different thresholds and an analysing process according to an embodiment of the present invention. In FIG. 10A a 3D rendering 1 as described above, is depicted having a threshold of zero. That is, all voxels are visible in the 3D rendering 1. Accordingly, the anatomical structure is hardly visible for the user 10 in the 3D rendering. Nevertheless, the MPR-views 3, 8 depicted in the 2D-frames 2, 7 are visible because the cropping bodies 9, 12 cut the 3D rendering 1 away. In addition, a first point 4, a second point 6 and a measuring path 5 are visible in FIGS. 10A and 10B. In FIG. 10B, the threshold is set to a value of 89/225. That is, all voxels having a value higher than 89 and lower than 225 are rendered so as to generate the 3D rendering 1. As a result, the anatomical structure can be better imagined. This example is intended to show how sensitively 3D rendering 1 reacts to the threshold setting. On the other hand, the MPR-views 3, 8 represent the ground truth of the 3D medical image data and are not dependent on any settings which may deteriorate the meaningfulness of the MPR-views 3, 8. Therefore, the inventive combination of both display formats exhibits an unknown accuracy and operator convenience.

Figure 11:
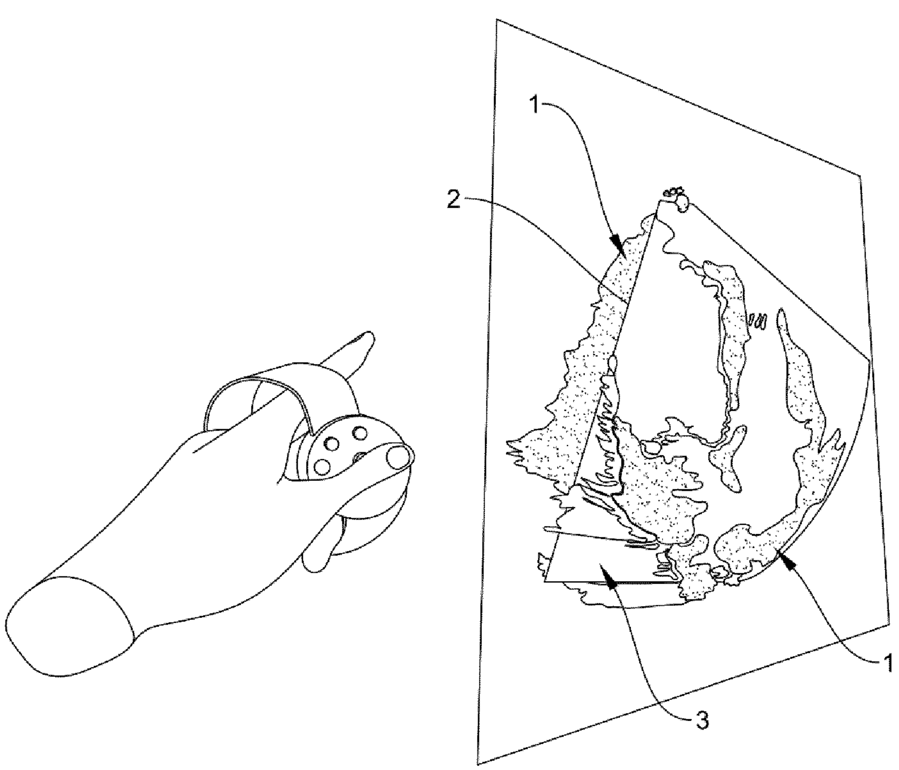
FIG. 11 shows a schematic representation of a calibration process according to an embodiment of the present invention.

Further, according to a further embodiment of the present invention, the accurateness of the MPR-views 3,8 is used to calibrate the 3D rendering 1. In FIG. 11 the 3D rendering 1 is depicted. Further, the 2D-frame 2 is provided in which the MPR-view 3 is depicted. In contrast to the previously described embodiments, in the present embodiment the cropping body (not depicted in FIG. 11) does not reach up to the 2D-frame 2. On the other hand, the cropping body 8 allows that the 3D rendering 1 partly reaches though the 2D-frame 2 and thus through the MPR-view 3. In other words, the cropping body is spaced apart from the 2D-frame by a predefined distance. This ensures that the user 20 can see the MPR-view 3 and the part of the 3D rendering 1 that is allowed to reach from the first side of the 2D-frame towards the user (i.e. this is dependent on the distance of the cropping body to the first side of the cropping body).

In the present embodiment, the user sees the MPR-view 3 as a black and white representation of the 3D medical image data at the first side of the 2D-frame. In addition, he sees the 3D rendering being erected from the first side of the 2D-frame (i.e. the 3D rendering 1 that extends through the 2D-frame). The outer contour of an intersection of the 3D rendering 1 and the MPR-view may be used to calibrate the threshold of the 3D rendering based on the MPR-view. In other words, the threshold is adapted such that said outer contour of the intersection fits to the contour depicted in the MPR-view. As a result, the threshold may be determined such that the 3D rendering 1 correctly represent the anatomical structure. This further improves the accuracy of analysing the 3D medical image data.

Figure 12:
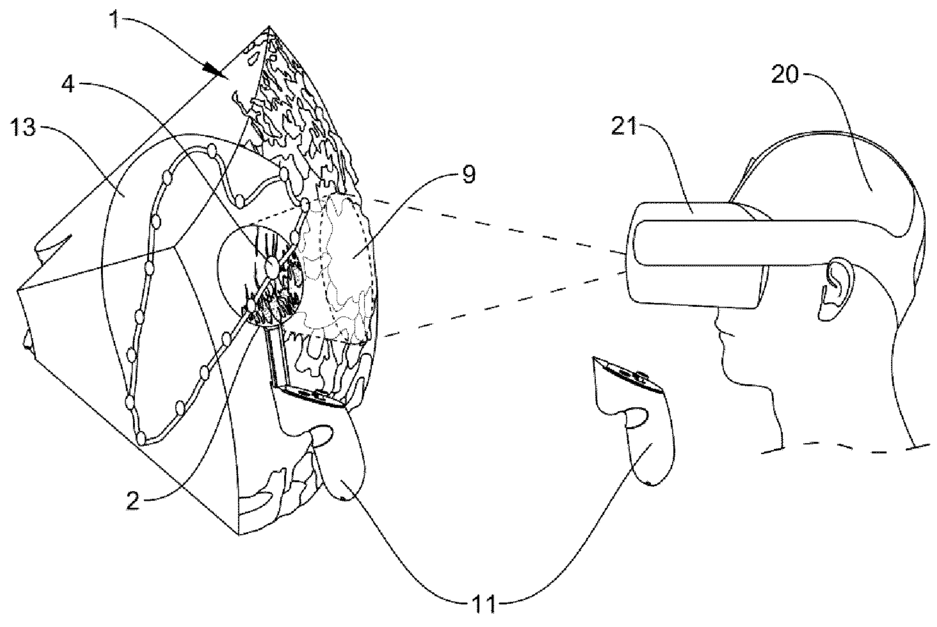
FIG. 12 shows a schematic representation of a adaption process according to an embodiment of the present invention.

In FIG. 12 a further embodiment of the present invention is schematically depicted. The present embodiment corresponds substantially to the embodiment of FIG. 7 with the difference that in the present embodiment a surface model 13 is depicted within the visualisation environment 10. The surface model 13 may be automatically generated based on the 3D medical image data. The surface model 13 may have been generated to correspond to a feature of the anatomical structure. Using the MPR-view 3, the user 20 can verify that the surface model 13 does indeed correctly correspond to said feature.

Figure 13:
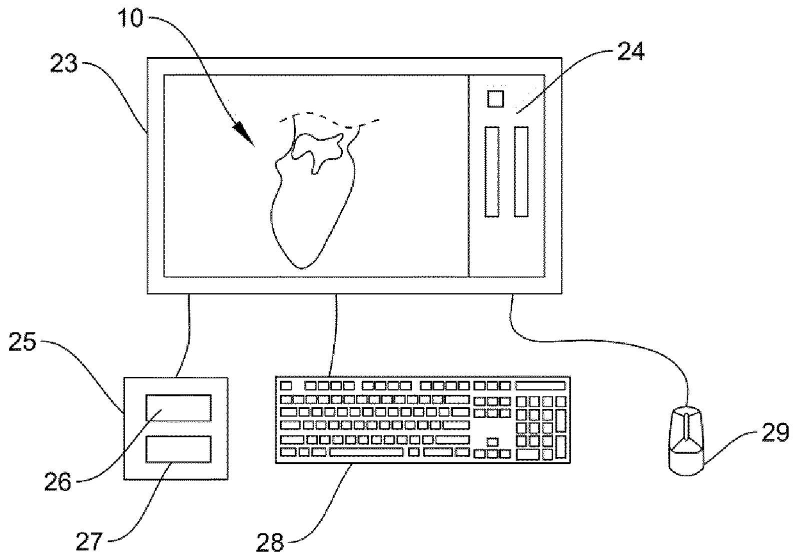
FIG. 13 shows a schematic representation of a 3D-medical image data evaluation device according to an embodiment of the present invention.

FIG. 13 shows a user interface according to a non-VR embodiment of the invention. In this setting, the visualisation environment 10 is on a conventional computer screen 23, and the visualisation is merely a rendering on the two-dimensional screen 23. The screen may comprise a panel 24 of buttons and sliders allowing the user to tilt, zoom, move or otherwise manipulate 3D rendering 1, the 2D-frame 2 etc. Also in such a user interface, it is useful tool to have a 3D rendering and a MPR-view 3. The display may be controlled by a computer 25, such as a PC, including a processor 26 and a hard disc 27. The user interface may have input tools such as a keyboard 28 and/or a mouse 29.

Figure 14:
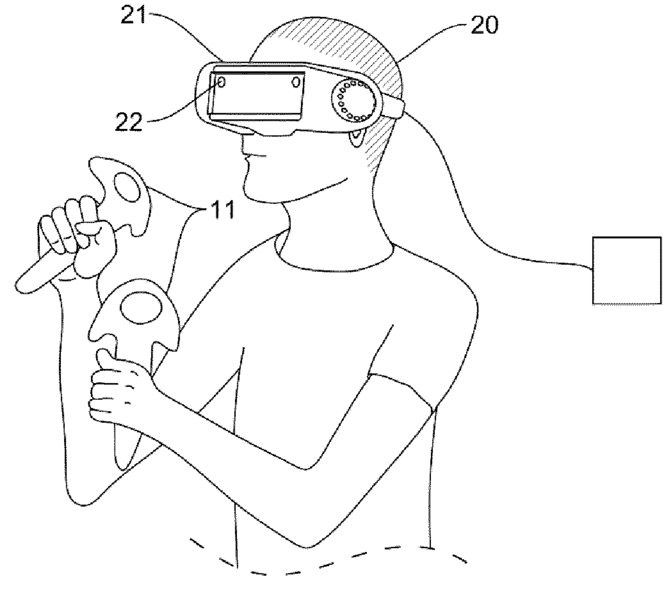
FIG. 14 shows a schematic representation of a 3D-medical image data evaluation device according to another embodiment of the present invention.

However, in a preferred embodiment, the user interface is a virtual reality interface, as shown in FIG. 14. Such interface is realised by a virtual reality headset 21 worn by a user 20. The headset 21 is connected to a computer 25, either through a cable or through wireless connection. Such virtual reality headset 21 includes internal displays, separate for each eye, as well as position sensors 22 which track the movement of the head. Such headset may also include cameras, in case an augmented reality environment is to be presented. Further, the user 20 is holding VR controllers 11 in his hands, wherein the controllers 11 also include position sensors (not shown) as well as buttons or other input elements. Such virtual reality controller 11 allows a user to grab and move an object displayed in the visualisation environment 5010 The VR headset may for example be an HTC VIVE headset and corresponding VR controllers.

While the invention has been illustrated and described in detail in the drawings and foregoing description, such illustration and description are to be considered illustrative or exemplary and not descriptive; the invention is not limited to the disclosed embodiments.

REFERENCE SIGNS

- 1 3D rendering
- 2,7 2D-frame
- 3,8 MPR visualisation
- 4 first point
- 5 Measurement path
- 6 second point
- 9,12 cropping body
- 11 controller
- 13 surface model
- 20 User
- 21 headset
- 22 position sensors
- 23 computer screen
- 24 panel
- 25 computer
- 26 processor
- 27 hard disc
- 28 keyboard
- 29 mouse

The invention claimed is:

1. Method for analysing 3D medical image data comprising:

receiving 3D medical image data of an anatomical structure;

generating a 3D rendering of the anatomical structure based on the 3D medical image data;

displaying the 3D rendering to a user in a visualisation environment;

receiving a user's command indicative of a first point on or within the 3D rendering;

providing a 2D-frame at a position in the visualisation environment in correspondence to the first point, wherein a first side of the 2D-frame is facing the user;

displaying an MPR-view within the 2D-frame, wherein the MPR-view is based on the 3D medical image data at the position of the 2D-frame and is sized so as to correspond to the size of the 2D-frame;

providing a transparent cropping body between the user and the first side of the 2D-frame so as to partly crop the 3D rendering; and receiving a user's command so as to change the size of the 2D-frame in the visualisation environment in response to a determination the 3D rendering is visible around the 2D-frame, wherein the MPR-view within the 2D-frame is updated to the new size of the 2D-frame, and wherein the size of the transparent cropping body is adapted to the new size of the 2D-frame.

2. Method according to claim 1, wherein the first side of the 2D-frame is facing the user so as to be at least substantially orthogonal to a viewing direction of the user.

3. Method according to claim 1, wherein the cropping body is positioned directly adjacent to the 2D-frame so as to crop the 3D rendering between the first side of the 2D-frame and the user, or wherein the cropping body is not directly adjacent to the 2D-frame and a ratio between the shortest distance of the cropping body to the 2D-frame and the perimeter of the 2D-frame is between 0.1 to 0.9, preferably between 0.1 and 0.6 and most preferably between 0.1 and 0.4.

4. Method according to claim 1, further comprising:

receiving a user's command so as to change the position of the 2D-frame in the visualisation environment, wherein the MPR-view within the 2D-frame is updated to the new position of the 2D-frame, and wherein the position of the transparent cropping body is adapted to the new position of the 2D-frame.

5. Method according to claim 1, wherein the 2D-frame is provided in an analysing plane extending in two dimensions through the 3D rendering, wherein the 2D-frame covers only a part of the analysing plane.

6. Method according to claim 1, wherein the transparent cropping body has an adaptable cross-section and the method further comprises the step of receiving a user's command indicative of a ratio in which the size of the cross-section changes with increasing distance from the 2D-frame.

7. Method according to claim 1, wherein the method further includes:

receiving a user's command so as to rotate and/or move the 3D rendering such that the 3D rendering has a new position and/or orientation within the visualisation environment, wherein the MPR-view within the 2D-frame is updated in correspondence to the new position of the 3D rendering, and/or wherein the shape and/or size of the cropping body is updated in correspondence to the new position of the 3D rendering.

8. Method according to claim 1, further comprising:

receiving a user's command indicative of a second point on or within the 3D rendering;

providing a second 2D-frame at a position in the visualisation environment in correspondence to the second point, wherein a first side of the second 2D-frame is facing the user, wherein the second 2D-frame is preferably at least substantially orthogonal to a viewing direction of the user, displaying a second MPR-view within the second 2D-frame, wherein the second MPR-view is based on the 3D medical image data at the position of the second 2D-frame and is sized so as to correspond to the size of the second 2D-frame; and providing a second transparent cropping body between the user and the first side of the second 2D-frame so as to partly crop the 3D rendering.

9. Method according to claim 1, further comprising the step of receiving a user's command so as to individually change the shape and/or size of the at least one 2D-frame.

10. Method according to claim 1, further comprising the step of:

receiving a user's command indicative of a measuring along a measuring path beginning at the first point set by the user, wherein the 2D-frame surrounds the first point and the measuring path, and adapts its size and/or shape dynamically to the measuring path, and receiving a user's command indicative of a position at which the measuring path ends.

11. Method according to claim 1, wherein the visualisation environment is a VR-environment or an AR-environment.

12. Method according to claim 1, wherein the method further comprises the step of receiving a user's command so as to provide a cropping plane extending through the whole 3D rendering and cropping the 3D rendering at one side of the cropping plane, wherein the cropping plane has an individual orientation and position within the visualisation environment.

13. Method according to claim 1, wherein the method further includes the step of automatically segmenting a surface model from the 3D medical image data, wherein the surface model corresponds to at least a part of the anatomical structure;

displaying the surface model within the visualisation environment, and receiving a user's command so as to adjust the surface model to the MPR-view within the 2D-frame.

14. An 3D medical image data evaluation device configured to perform the method according to claim 1, the evaluation device comprising:

an interface for receiving 3D medical image data, a computing unit for performing the method according to claim 1, and a visualisation device for providing the visualisation environment and for displaying at least the 3D rendering and the 2D-frame.

15. A non-transitory computer readable medium storing instructions that in response to execution on a processor cause the processor to:

receive 3D medical image data of an anatomical structure;

generate a 3D rendering of the anatomical structure based on the 3D medical image data;

display the 3D rendering to a user in a visualisation environment;

receive a user's command indicative of a first point on or within the 3D rendering;

provide a 2D-frame at a position in the visualisation environment in correspondence to the first point, wherein a first side of the 2D-frame is facing the user;

display an MPR-view within the 2D-frame, wherein the MPR-view is based on the 3D medical image data at the position of the 2D-frame and is sized so as to correspond to the size of the 2D-frame;

provide a transparent cropping body between the user and the first side of the 2D-frame so as to partly crop the 3D rendering; and receive a user's command so as to change the size of the 2D-frame in the visualisation environment in response to a determination the 3D rendering is visible around the 2D-frame, wherein the MPR-view within the 2D-frame is updated to the new size of the 2D-frame, and wherein the size of the transparent cropping body is adapted to the new size of the 2D-frame.

* * * * *